United States Patent [19]
Thal

[11] Patent Number: 5,709,708
[45] Date of Patent: Jan. 20, 1998

[54] CAPTURED-LOOP KNOTLESS SUTURE ANCHOR ASSEMBLY

[76] Inventor: Raymond Thal, 11321 Bright Pond La., Reston, Va. 22094

[21] Appl. No.: 792,738

[22] Filed: Jan. 31, 1997

[51] Int. Cl.⁶ ................................................. A61B 17/04
[52] U.S. Cl. ........................................................ 606/232
[58] Field of Search .......................... 606/232, 72–75, 606/219, 224

[56] References Cited

U.S. PATENT DOCUMENTS

| | | |
|---|---|---|
| 4,007,743 | 2/1977 | Blake . |
| 4,532,926 | 8/1985 | O'Holla . |
| 4,537,185 | 8/1985 | Stednitz . |
| 4,632,101 | 12/1986 | Freedland . |
| 4,721,103 | 1/1988 | Freedland . |
| 4,870,957 | 10/1989 | Goble et al. . |
| 4,898,156 | 2/1990 | Gatturna et al. . |
| 4,946,468 | 8/1990 | Li . |
| 5,013,316 | 5/1991 | Goble et al. . |
| 5,037,422 | 8/1991 | Hayhurst et al. . |
| 5,084,050 | 1/1992 | Draenert . |
| 5,102,421 | 4/1992 | Anspach, Jr. . |
| 5,141,520 | 8/1992 | Goble et al. . |
| 5,192,303 | 3/1993 | Gatturna et al. . |
| 5,207,679 | 5/1993 | Li . |
| 5,224,946 | 7/1993 | Hayhurst et al. . |
| 5,236,445 | 8/1993 | Hayhurst et al. . |
| 5,258,016 | 11/1993 | DiPoto et al. . |
| 5,356,413 | 10/1994 | Martins et al. . |
| 5,358,511 | 10/1994 | Gatturna et al. . |
| 5,370,661 | 12/1994 | Branch . |
| 5,370,662 | 12/1994 | Stone et al. . |
| 5,372,146 | 12/1994 | Branch . |
| 5,372,599 | 12/1994 | Martins . |
| 5,383,905 | 1/1995 | Golds et al. . |
| 5,400,805 | 3/1995 | Warren . |

Primary Examiner—Gary Jackson
Attorney, Agent, or Firm—Hoffman, Wasson & Gitler

[57] ABSTRACT

An enhanced knotless suture anchor assembly having a snag element or recess attached to, or formed in, an anchor assembly, for capturing a looped section of the suture element for enhanced knotless surgical soft tissue reattachment to bone.

10 Claims, 2 Drawing Sheets

CAPTURED-LOOP KNOTLESS SUTURE ANCHOR ASSEMBLY

BACKGROUND OF THE INVENTION

1. Field of the Invention

The present invention relates to devices or assemblies used in tissue repair. More particularly, the assembly is an enhanced device that enables the attachment together or repair of portions of biological tissue, such as tendons or ligaments, on a bone surface.

2. Description of the Background Art

Soft tissues, such as tendons and ligaments, generally are attached to bone by small collagenous fibers. These connections are strong but permit the tendons and ligaments to be flexible. When a tissue is torn away from the bone and requires repair, a surgeon is often required to repair the detached soft tissue with sutures which are passed through bone tunnels and tied. A number of devices have been developed for securing a ligament or tendon to a bone mass. These devices can be used in place of bone tunnelling techniques. These attachment devices are usually inserted through extensive surgical incisions and, in some circumstances, by arthroscopic surgical techniques. The use of bone tunnels for repair can be difficult and generally require large open incisions. Recently, through the advent of endoscopic surgery, where the surgeon looks into a joint cavity with a telescope, there has been a trend to repair soft tissues back to bone through small incisions called portals. The unique knotless suture anchor assemblies described herein facilitate this difficult and precise procedure.

A variety of devices are available for attaching objects to bone, such as screws, staples, cement, suture anchors, and sutures alone. These devices have been used to attach soft tissue, such as ligaments, tendons, muscles, as well as objects such as protheses, to bone. A suture anchor is a device which utilizes small anchors with suture materials attached thereto. A device, such as a screw, is inserted into the bone mass and anchored in place. After insertion of the anchor, the attached suture is passed through the tissue to be repaired. The tying of a knot in the suture is then required to secure the tissue to the bone. The process of passing the anchored suture through the soft tissue and tying a knot is time consuming and difficult to undertake in the tight space encountered during endoscopic surgery and sometimes even in conventional open surgery.

One example of a suture anchor assembly is disclosed in U.S. Pat. No. 5,370,662, wherein an anchor assembly includes a pre-threaded suture positioned at its posterior. First the anchor is inserted into the bone mass. The attached suture is then passed through the tissue for reattachment. The surgeon is required to tie a knot with the suture to complete the surgical process. Some suture anchors can be passed through the soft tissue first and then into the bone. Most suture anchors need to be inserted into the bone first. Only after this has been accomplished can the sutures be passed through the soft tissue. Alternatives to this procedure include non-suture soft tissue anchor systems. A few of these systems, such as those disclosed in U.S. Pat. Nos. 5,013,316 and 4,532,926, can be used arthroscopically but fixation with these devices may not be as secure as that achieved with sutures. Only a few points of fixation are possible with the non-suture type anchor since the device is relatively large. Therefore suture devices are more favorable. This type of non-suture staple device is disadvantageous in that it has been known to crack the bone during deployment, or accidentally transect the object being attached to the bone. In addition, the device itself has been known to crack or break during or after deployment.

U.S. Pat. Nos. 5,037,422; 5,224,946; and 5,236,445 all disclose bone anchor configurations for attaching sutures within openings formed in bones during joint reconstructive surgery and endoscopic surgical procedures. With all these intricate procedures, the suture itself must be inserted through a tissue mass and tied with a surgical knot to repair the soft tissue to bone.

It is an object of the present invention to provide a knotless suture anchor assembly which is easy to use and install.

Another object of the present invention is to provide a suture anchor assembly which allows for secure attachment of soft tissue to a bone mass without the use or requirement of tying a knot.

Still another object of the present invention is to provide a suture anchor assembly which is compact and allows a surgeon to easily guide the anchor means into the bone mass, or anchoring sleeve if desired, to enhance the security of the repair.

A primary feature of the present invention is to provide a unique snag-type means which is provided to facilitate engagement of the anchor means with a continuous suture loop, for drawing soft tissue to the bone mass, once the anchor means is deposited directly in the bone or in a hollow anchoring sleeve.

SUMMARY OF THE INVENTION

In accordance with the above objects, the present invention is an enhanced knotless suture anchor assembly for attachment or reattachment of biological soft tissue to bone. The unique enhanced knotless suture anchor assembly includes an anchor means which can either be installed into a bone mass or into a hollow anchoring sleeve which has been installed into a bone mass. The hollow anchoring sleeve or anchor means can have varying shaped exteriors for secure capturing or engagement with a bone mass.

Incorporated by reference are U.S. Pat. Nos. 4,007,743; 4,632,101; 4,721,103; 4,870,957; 4,898,156; 4,946,468; 5,084,050; 5,102,421; 5,141,520; 5,192,303; and 5,207,679, which all illustrate varying exterior structures which may embody the anchor means or anchoring sleeve of the invention.

Further, if desired, the hollow anchoring sleeve can contain a collar on the rear portion or rear side to control the depth of sleeve insertion into the bone and prevent excessive insertion depth. The anchor means of the assembly has a first end or configuration which allows for secure capturing of either the hollow anchoring sleeve or the bone mass and a component for securing the suture element or sliding continuous loop of the suture element. The first end can be pointed or frustoconical in shape. The anchor means can be ribbed, beaded, threaded, or expandable on its exterior surface or further can contain one or more prongs for secure mating with the anchoring sleeve or bone mass.

The anchor means has located thereon unique snag means in the shape of a hook, or other type projection, or a recess cut into the anchor, or a slit cut into an existing opening in the anchor, for engaging a continuous loop portion of the suture element.

The suture element can be attached permanently to the rear end of the anchor means or can be attached in a hole thereon in a continuous loop configuration. The hook portion or projection can be made of the same material as the entire anchor means or a different material, as desired. The anchor means can be inserted during an open procedure, or an endoscopic procedure. In the preferred method, the suture element is first passed through the soft tissue and attached or connected to the snag-type means and subsequent to such steps, the anchor means is then inserted into the bone mass or into the hollowing anchoring sleeve which has been inserted into the bone mass.

Secondly, the anchor means can be directly pierced through the tissue and the continuous loop of the suture element can then be attached to the snag means followed by the engagement of the anchor means to the bone mass or hollow anchoring sleeve.

Numerous other features of various embodiments of the enhanced knotless suture anchor assembly will be apparent from the following detailed description and the accompanying drawings.

DETAILED DESCRIPTION OF THE PRESENT INVENTION

Figure 1:
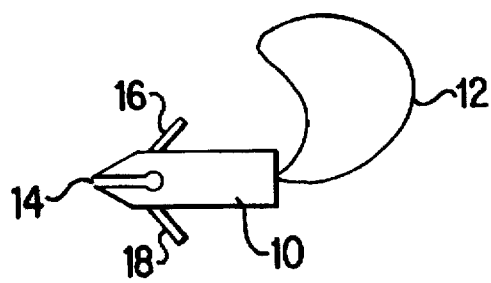
FIG. 1 is a perspective view of an anchor means with a continuous loop suture element and a snag recess.

Referring to FIG. 1, the enhanced knotless suture anchor assembly of the present invention contains an anchor means 10, a suture element 12 and a snag means 14. The anchor means in the figure also contains prongs 16 and 18 which facilitate the attachment of the anchor means 10 to a bone mass. The device can also contain, or be configured with, umbrella spokes, it can contain threads, be expandable, or have any other type of engaging features on its exterior for secure attachment with a bone mass. All of these exterior attachment features are known to the industry and incorporated herein by reference.

Figure 2:
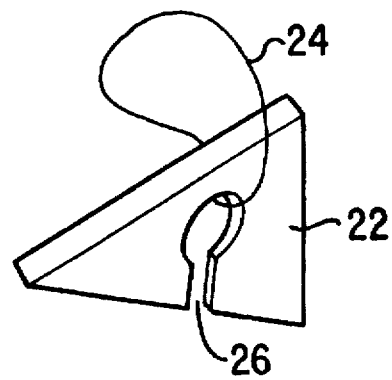
FIG. 2 is a perspective view of a wedge type anchor means having a recess snag means with a continuous loop suture element.

FIG. 2 illustrates an alternate embodiment of the enhanced knotless suture assembly. Depicted is a wedge-like anchor means 22, a suture element 24 and a snag means 26.

Figure 3:
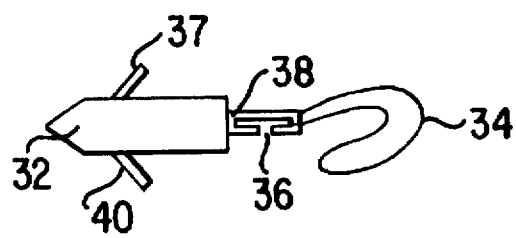
FIG. 3 is a pronged type anchor with a perspective view of an alternate embodiment of an anchor means with suture element of the present invention.

FIG. 3 illustrates another alternate embodiment of the present invention. Depicted is an anchor means 32, a continuous suture loop 34 and a snag means 36 located on a rear hub 38 of the anchor means 32. Also pictured in this embodiment are two prongs 39 and 40 for secure attachment or mating with a bone mass or hollow anchor assembly.

In FIGS. 1, 2 and 3 the suture elements 12, 24 and 34 are all continuous loops. These elements may have more than one loop or be permanently affixed to the anchor means at one of its ends.

Figure 4:
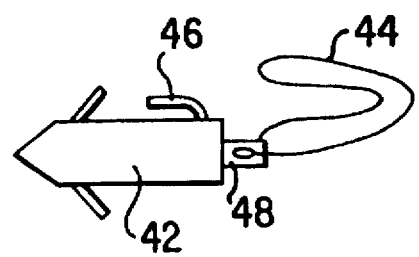
FIG. 4 is an alternate embodiment of an anchor means with suture element of the present invention.

FIG. 4 is a depiction of an alternate embodiment of the present invention. Depicted is an anchor means 42, a suture element 44 and a snag means 46 for capturing the suture element. In this embodiment, the continuous suture element 44 is engaged at a rear hub 48 of the anchor means 42.

Figure 5A:
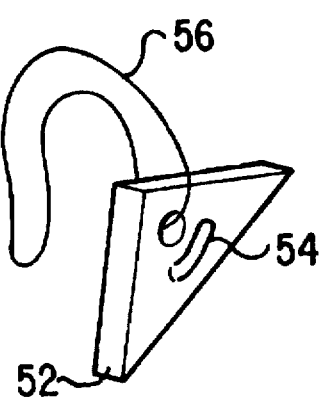
FIGS. 5A and 5B are alternate embodiments of an anchor means with suture element of the present invention.
Figure 5B:
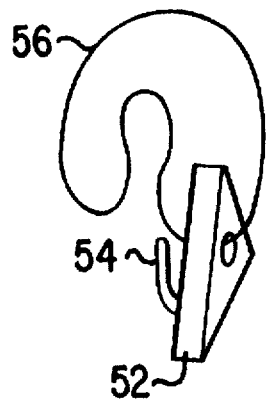

FIG. 5A and 5B illustrate alternate embodiments of the invention wherein a wedge-like anchor means 52 includes a snag means 54 and a suture element 56.

In all of the embodiments, either the anchor means or the suture element can be passed through the tissue first and then the continuous loop of the suture element is engaged into the recess or onto the projection or hook means thus capturing the suture loop. The anchor is then inserted into either a hollow anchoring sleeve or a bone mass thereby approximating the soft tissue to the bone mass. It is also within the contemplation of the present invention to configure the anchor means such as is disclosed by U.S. Pat. Nos. 4,632,101; 4,721,103; 4,898,156; 5,207,679; 4,946,468; and 5,192,303. A good depiction of the various configuration can be seen in applicant's own U.S. Pat. No. 5,569,306. These patents are incorporated by reference and fall within the contemplation of the present invention for methods or means for anchoring the anchor means or hollow anchoring sleeve to a bone mass.

Figure 6:
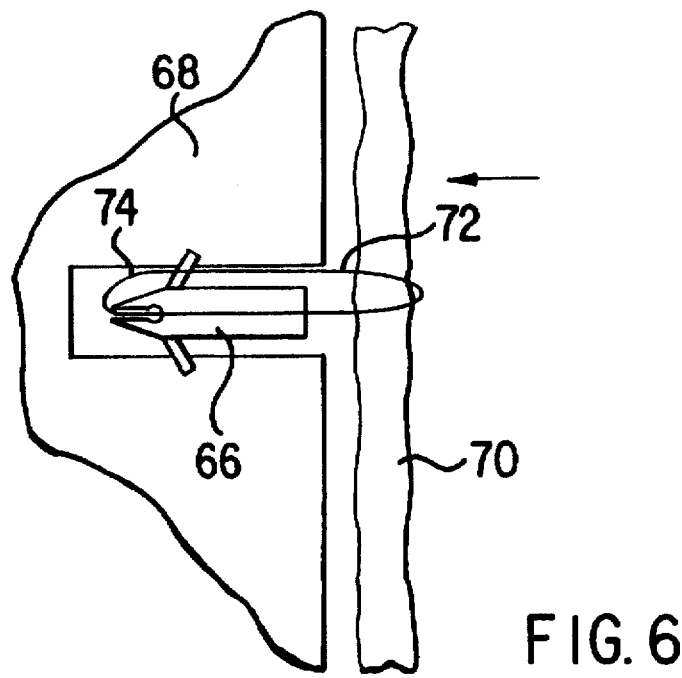
FIG. 6 illustrates the procedure for attachment of tissue to bone mass for the embodiment outlined in FIG. 1.
Figure 7:
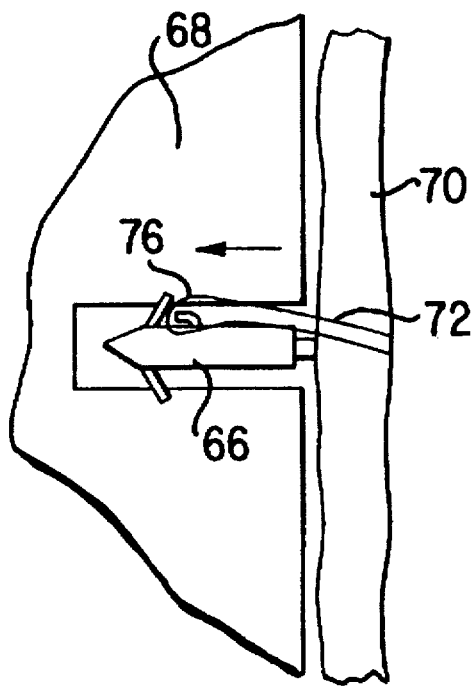
FIG. 7 illustrates the procedure for attachment of tissue to bone mass for the embodiment as outlined in FIG. 4.

FIGS. 6 and 7 depict the embodiments set forth in FIGS. 1 and 4 wherein a hollow anchoring sleeve has an anchor means 66 inserted into a bone mass 68 for drawing a tissue 70 into secure engagement therewith. In these embodiments, the suture element 72 is first passed through the tissue element 70 and then engaged onto the recess 74 of FIG. 6 or projection 76 of FIG. 7 for engagement with the anchor means.

In both of these situations, the anchor can be passed through the tissue first, rather than having the suture element being passed through the tissue.

In many situations throughout the discussion above, the terminology secure attachment of soft tissue to bone has been used. Such terminology refers to the attachment or reattachment of tissue to a bone mass through the insertion of an anchor means into the bone mass or a hollow anchoring sleeve. In the one situation, the anchor means can seat into the hollow anchoring sleeve in a one step mating procedure or be inserted and ratcheted down in a step wise fashion into the sleeve. In the second situation, the anchor means will be directly inserted into the bone mass and ratcheted down drawing the tissue to the bone mass as well. In addition to the shapes illustrated for the snag means, such can take the form of anything which would allow the continuous loop portion of the suture to be captured by the hook, projection, slit or recess in the anchor means. The suture element can be made up us a known suture material, or it can be made of polymer materials, or can be formed of bioabsorbable material such as a polylactide polymer.

While a preferred embodiment of the invention is illustrated, it should be understood that the present disclosure is made by way of example and that variations to the structure shown and its use are possible within the scope of this disclosure without departing from the subject matter coming within the scope of the claims.

What is claimed is:

1. A knotless suture anchor assembly for attachment of tissue to a bone mass, said assembly comprising:
   a) an anchor means for attachment to said bone mass;
   b) a suture element connected to said anchor means having a continuous loop formed along its length; and
   c) a snag means located on said anchor means, wherein said snag means captures said continuous loop of said suture element to draw said tissue into secure attachment with said bone mass.

2. A knotless suture anchor assembly as claimed in claim 1, wherein said snag means is a recess formed in said anchor means to capture said continuous loop of said suture element and allow said tissue to be drawn to said bone mass.

3. A knotless suture anchor assembly as claimed in claim 1, wherein said snag means is an external hook or projection for capturing said continuous loop of said suture element and allowing said tissue to be drawn to said bone mass.

4. A knotless suture anchor assembly as claimed in claim 1, wherein said suture element is permanently attached to said anchor means.

5. A knotless suture anchor assembly as claimed in claim 1, wherein said suture element is a continuous loop passing through said anchor means but not permanently affixed to said anchor assembly.

6. A knotless suture anchor assembly as claimed in claim 1, further comprising a hollow anchoring sleeve for installation and attachment to said bone mass for receiving said anchor means.

7. A method for the attachment of tissue to a bone mass utilizing said knotless suture anchor assembly as claimed in claim 1, comprising the steps of:
 a) passing said suture element through said tissue;
 b) capturing said continuous loop of said suture element with said snag means of said anchor means; and
 c) installing said anchor means into said bone mass, for attachment of said tissue to said bone mass.

8. A method for the attachment of tissue to a bone mass utilizing said knotless suture anchor assembly as claimed in claim 6, comprising the steps of:
 a) installing said hollow anchoring sleeve into said bone mass;
 b) passing said suture element through said tissue;
 c) capturing said continuous loop of said suture element with said snag means of said anchor means; and
 d) installing said anchor means into said hollow anchoring sleeve, for secure attachment of said tissue to said bone mass.

9. A method for the attachment of tissue to a bone mass utilizing said knotless suture anchor assembly as claimed in claim 1, comprising the steps of:
 a) passing said anchor means through said tissue;
 b) capturing said continuous loop of said suture element with said snag means of said anchor means; and
 c) installing said anchor means into said bone mass, for secure attachment of said tissue to said bone mass.

10. A method for the attachment of tissue to a bone mass utilizing said knotless suture anchor assembly as claimed in claim 6, comprising the steps of:
 a) installing said hollow anchoring sleeve into said bone mass;
 b) passing said anchor means through said tissue;
 c) capturing said continuous loop of said suture element with said snag means of said anchor means; and
 d) installing said anchor means into said hollow anchoring sleeve, for secure attachment of said tissue to said bone mass.

* * * * *